United States Patent [19]

Fischer et al.

[11] Patent Number: 4,762,944

[45] Date of Patent: Aug. 9, 1988

[54] BUTENOIC ACID DERIVATIVES, PHARMACEUTICAL COMPOSITIONS CONTAINING THEM AND PROCESS FOR PREPARING SAME

[75] Inventors: János Fischer; László Dobay; Elémer Ezer; Judit Matuz; Laszló Szporny; Tibor Wagner, all of Budapest, Hungary

[73] Assignee: Richter Gedeon Vegyeszeti Gyar RT, Budapest, Hungary

[21] Appl. No.: 25,339

[22] Filed: Mar. 13, 1987

[30] Foreign Application Priority Data

Apr. 1, 1986 [HU] Hungary .............................. 1332/86

[51] Int. Cl.⁴ ............................................. C07C 69/76
[52] U.S. Cl. ....................................................... 560/051
[58] Field of Search ........................... 560/51; 514/532

[56] References Cited

PUBLICATIONS

Bowden, K. J. Chem. Soc. B (1)156–160 1971; CA74(13); 63664t.

Bowden, K et al., Advan. Chem. Ser. 114(Biol Correl–Hansch Approach Symp.)130–140, 1972 CA78(13): 80361S.

Anderson et al, Biochem. Biophys. Acta 703(2), 204–211, 1982, CA 97(1)2728 V.

*Primary Examiner*—Paul J. Killos
*Attorney, Agent, or Firm*—Karl F. Ross; Herbert Dubno

[57] ABSTRACT

The invention relates to novel butenoic acid derivatives of the general formula (Ia) having E-configuration

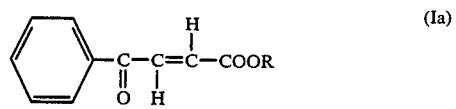

as well as to their Z-izomers of the general formula

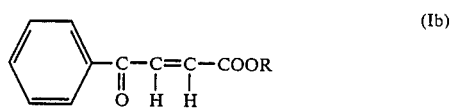

wherein R stands for a (−)-menthyl or a (+)-menthyl group. as well as pharmaceutical compositions containing these compounds.

The novel butenoic acid derivatives of the general formulae (Ia) and (Ib) possess valuable pharmacological properties, mainly gastric cytoprotective effect.

4 Claims, No Drawings

BUTENOIC ACID DERIVATIVES, PHARMACEUTICAL COMPOSITIONS CONTAINING THEM AND PROCESS FOR PREPARING SAME

The invention relates to novel butenoic acid derivatives of the formula (Ia) having E-configuration

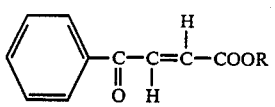

as well as to their Z-isomers of the formula (Ib)

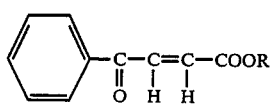

wherein R stands for a (−)-methyl or a (+)-menthyl group as well as pharmaceutical compositions containing these compounds.

According to an other aspect of the invention, there is provided a process for the preparation of the new compounds of the formulae (Ia) and (Ib).

The novel menthyl esters of formula (Ia) are prepared by reacting the known substituted butenoic acid of the formula (II) [O. Grumit et al. Org. Synth. Coll. 3, 109 (1955)] or an activated carboxylic acid derivative thereof with (−)-menthol or (+)-menthol of formula (III) or with an alkaline metal salt thereof in a manner known per se. Alternatively, acetophenone may be reacted with (−)- or (+)-menthyl glyoxylate.

The Z-isomers of formula (Ib) may be obtained from the compounds of formula (Ia) by isomerization, e.g. by irradiation with ultraviolet light.

The novel butenoic acid derivatives of the invention possess valuable pharmacological properties, mainly a cytoprotective effect.

The gastric cytoprotective action was tested by using the method of A. Robert [Gastroenterology 77, 761–767 (1979)] as follows.

Rats weighing 120 to 150 g were starved for 24 hours, then the compounds under test were administered to the animals in an amount of 2, 5, 10 or 20 mg/kg, respectively through a gastric tube. Thirty minutes after the administration, a so-called necrotizing material (50 ml of ethanol containing 1 ml of concentrated hydrochloric acid) was given to the animals similarly through the gastric tube. The members of the control group did not receive any cytoprotective compound.

After one hour the animals were killed, their stomaches were removed, the length in millimeters of the haemorrhagic laesions found in the glandular part of the stomach was measured and averaged to each stomach. The ratio of the cytoprotection was given as compared to the values measured in the control group.

In the following Table 1, the data obtained with the most active isomer, i.e. (−)-menthyl (E)-4-oxo-4-phenyl-2-butenoate are summarized. For comparison, the values obtained with sucralfate [saccharose-octakis(hydrogen sulfate)-aluminum complex; see, C.A. 68, 20831d (1968)], a known cytoprotective agent are also shown in Table 1.

TABLE 1

| Test compound | Dose mg/kg p.o. | Cytoprotection as % of the control |
|---|---|---|
| (−)-Menthyl (E)-4-oxo-4-phenyl-2-butenoate | 1 | 0 |
| | 2 | 16 |
| | 5 | 65 |
| | 10 | 76 |
| | 20 | 85 |
| Sucralfate | 50 | 41 |
| | 400 | 62 |
| | 800 | 63 |

It is obvious from the Table that a definitive cytoprotective effect was obtained by substantially higher doses of the reference drug as compared to the effective doses of the compound according to the invention.

The acute toxicity of the compound of the invention was also determined and the compound proved to be non-toxic even at an oral dose of 2000 mg/kg.

According to the invention, the new menthyl esters of the formulae (Ia) and (Ib) are prepared (a) by esterifying the substituted butenoic acid of the formula (II)

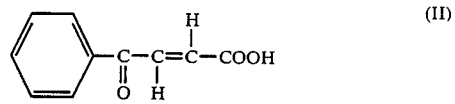

or an activated carboxylic acid derivative thereof with (−)-menthol or (+)-menthol of the formula (III)

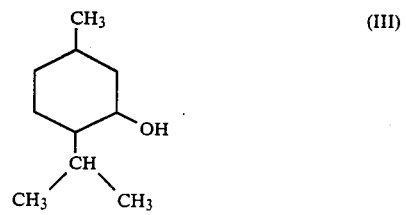

or with an alkaline metal salt thereof in a manner known per se, or (b) by reacting acetophenone with (−)- or (+)-menthyl glyoxylate in the presence of acetic acid anhydride or an other dehydrating agent and recovering the thus-prepared product of the formula (Ia) prepared by using either process (a) or (b) or if desired, isomerizing to the compound of the formula (Ib).

According to process (a) of the invention, the substituted butenoic acid of the formula (II) or an activated carboxylic acid derivative thereof is esterified. The carboxylic acid group may preferably be activated by using a carbodiimide, particularly by using dicyclohexylcarbodiimide. A lower alkyl ester of the acid of the formula (II) may also be used as an activated derivative.

When the acid of the formula (II) is activated by using a carbodiimide, the esterification is carried out by using (−)-menthol or (+)-menthol in the presence of a suitable catalyst, in a solvent which is inert to the reaction. Suitable inert solvents are: benzene and its homologs; chlorinated hydrocarbons such as dichloromethane, chloroform and dichloroethane; various ethers such as diethyl ether, tetrahydrofuran and dioxane; as well as ethyl acetate and the like. 4-Dimethylaminopyridine and pyridine are preferred catalysts. The reaction is carried out at a temperature between 0° C. and 50° C.

When the activated derivative is a lower alkyl ester such as the methyl, ethyl or butyl ester of the compound of formula (II), then an alkaline metal mentholate preferably sodium mentholate having the appropriate configuration is used as reactant.

According to process (b) of the invention, acetophenone is reacted with (−)-menthyl glyoxylate or (+)-menthyl glyoxylate. This reaction is accomplished in the presence of acetic anhydride or an other dehydrating agent.

If desired, the thus-obtained product may be converted to the Z-isomer of the formula (Ib). This isomerization can preferably be achieved by irradiation with ultraviolet light.

The invention is illustrated in detail by the following non-limiting Examples.

EXAMPLE 1

(−)-menthyl-(E)-4-oxo-4-phenyl-2-butenoate 4.43 g (0.028 mole) of (−)-menthol and 0.34 g (0.003 mole) of 4-dimethylaminopyridine are added to a solution of 5.0 g (0.028 mole) of (E)-4-oxo-4-phenyl-2-butenoic acid in 60 ml of anhydrous dichloromethane. After cooling the solution to 0° C. the solution of 5.86 g (0.028 mole) of N,N-dicyclohexylcarbodiimid in 20 ml of anhydrous dichloromethane is added. The mixture is stirred at 0° C. for half an hour, then at room temperature for one hour. The precipitated dicyclohexylurea is filtered and the dichloromethane filtrate is successively extracted: (a) 3 times with 15 ml of 1 N aqueous hydrochloric acid solution each; (b) once with 15 ml of water; (c) 3 times with 15 ml of saturated aqueous sodium carbonate solution each; and (d) once with 20 ml of saturated aqueous sodium chloride solution. The organic phase is filtered through a compacted silica gel layer, dried over anhydrous magnesium sulfate and evaporated to give 8.38 g (94% yield) of a dark-brown oil which is purified by column chromatography (by using Kieselgel 60, 0.040–0.063 mm as adsorbent and dichloromethane as eluant). The named compound is obtained in a yield of 6.5 g, $R_f=0.58$ (dichloromethane); $[\alpha]_D^{25}=-63.3°$ (c=2.1, chloroform).

EXAMPLE 2

(+)-Menthyl-(E)-4-oxo-4-phenyl-2-butenoate 4.43 g (0.028 mole) of (+)-menthol and 0.34 g (0.003 mole) of 4-dimethylaminopyridine are added to a solution of 5.0 g (0.028 mole) of (E)-4-oxo-4-phenyl-2-butenoic acid in 60 ml of anhydrous dichloromethane. After cooling the solution to 0° C., a solution of 5.86 g (0.028 mole) of N,N-dicyclohexylcarbodiimide in 20 ml of anhydrous dichloromethane is added. The mixture is stirred at 0° C. for 30 minutes, then at room temperature for one hour. The reaction mixture is worked up as described in Example 1 to give the crude product as a dark-brown oil in a yield of 8.1 g (91%) which is purified by using column chromatography as described in Example 1. The named compound is obtained in a yield of 6.7 g, $R_f=0.78$ (dichloromethane); $[\alpha]_D^{25}=+65°$ (c=2.0, chloroform).

EXAMPLE 3

(−)-Menthyl (Z)-4-oxo-4-phenyl-2-butenoate

A solution of 3.0 g (0.009 mole) of (−)-menthyl (E)-4-oxo-4-phenyl-2-butenoate in 100 ml of anhydrous acetone is irradiated with ultraviolet light. After an irradiation lasting 3 hours the solution is evaporated and the residue is recrystallized from n-hexane to give the named compound in a yield of 1.9 g, m.p.: 85°–87° C. $[\alpha]_D^{25}=-74.7°$ (c=1, chloroform).

EXAMPLE 4

(+)-Menthyl (Z)-4-oxo-4-phenyl-2-butenoate

A solution of 2.0 g (0.006 mole) of (+)-menthyl (E)-4-oxo-4-phenyl-2-butenoate in 100 ml of anhydrous acetone is irradiated with ultraviolet light for 2 hours, then evaporated under reduced pressure and the residue is recrystallized from n-hexane to give the named compound in a yield of 1.2 g, m.p.: 85°–87° C., $[\alpha]_D^{25}=+82.5°$ (c=1, chloroform).

We claim:

1. A Butenoic acid derivative of the formula (Ia) having E-configuration

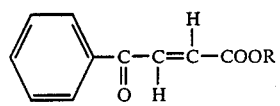

or a Z-isomer of the formula (Ib)

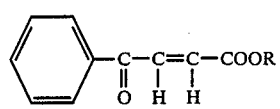

wherein

R is a (−)-menthyl or a (+)-menthyl group.

2. A cytoprotective pharmaceutical composition which comprises as active ingredient a therapeutically effective amount of a butenoic acid derivative as defined in claim 1, in admixture with a pharmaceutical carrier and/or additive.

3. A process for the preparation of the novel butenoic acid derivatives of the formula (Ia)

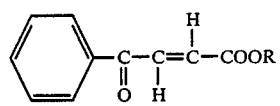

or a Z-isomer thereof of the formula (Ib)

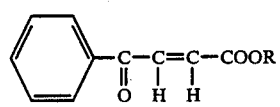

wherein

R is (−)-menthyl or a (+)-menthyl, which comprises reacting acetophenone with (−)- or (+)-menthyl glyoxylate in the presence of acetic acid anhydride or an other dehydrating agent and recovering the thus-prepared product of the formula (Ia) or isomerizing said product to the compound of the formula (Ib).

4. A cytoprotective method of treatment which comprises administering to an animal subject at risk of cytotoxicity an effective amount of at least one derivative as defined in claim 1.

* * * * *